(12) United States Patent
Sun et al.

(10) Patent No.: US 10,814,037 B2
(45) Date of Patent: Oct. 27, 2020

(54) METHOD FOR PREPARING CELL GROWTH SCAFFOLD HAVING STRUCTURAL MEMORY PROPERTIES

(71) Applicant: Beijing Ruijian Gaoke Biotechnology Co., Ltd., Beijing (CN)

(72) Inventors: Wenquan Sun, Beijing (CN); Senli Huang, Beijing (CN)

(73) Assignee: BEIJING RUIJIAN GAOKE BIOTECHNOLOGY CO., LTD., Beijing (CN)

(*) Notice: Subject to any disclaimer, the term of this patent is extended or adjusted under 35 U.S.C. 154(b) by 170 days.

(21) Appl. No.: 16/064,798

(22) PCT Filed: Dec. 24, 2016

(86) PCT No.: PCT/CN2016/111926
§ 371 (c)(1),
(2) Date: Jun. 21, 2018

(87) PCT Pub. No.: WO2017/107997
PCT Pub. Date: Jun. 29, 2017

(65) Prior Publication Data
US 2018/0369450 A1 Dec. 27, 2018

(30) Foreign Application Priority Data
Dec. 25, 2015 (CN) .......................... 2015 1 0986265

(51) Int. Cl.
*A61L 27/36* (2006.01)
*A61L 27/24* (2006.01)
(Continued)

(52) U.S. Cl.
CPC .......... *A61L 27/3687* (2013.01); *A61L 27/24* (2013.01); *A61L 27/36* (2013.01); *A61L 27/3691* (2013.01);
(Continued)

(58) Field of Classification Search
None
See application file for complete search history.

(56) References Cited

U.S. PATENT DOCUMENTS

| | | | | |
|---|---|---|---|---|
| 4,320,201 A | * | 3/1982 | Berg | .................... A61K 8/0208 435/265 |
| 8,785,389 B2 | * | 7/2014 | Brown | .................... A61L 27/24 424/70.14 |

(Continued)

FOREIGN PATENT DOCUMENTS

| CN | 1407002 A | 4/2003 |
|---|---|---|
| CN | 101507831 A | 8/2009 |

(Continued)

OTHER PUBLICATIONS

International Search Report of PCT/CN2016/111926, dated Mar. 31, 2017.

(Continued)

*Primary Examiner* — Kevin K Hill
*Assistant Examiner* — James Joseph Graber
(74) *Attorney, Agent, or Firm* — Banner & Witcoff, Ltd.

(57) ABSTRACT

Disclosed is a method for preparing a cell growth scaffold having a structural memory feature, comprising a step of preparing a micro-fibrous or flocculent acellular tissue matrix material; a step of preparing an acidification-treated hydrogel-like acellular tissue matrix particles; proportionally mixing the micro-fibrous or flocculent acellular tissue matrix material with the acidification-treated hydrogel-like acellular tissue matrix particles, followed by injection-molding, freezing treatment, radiation treatment, and ultimately preparing a porous cell growth scaffold that can be stored at room temperature. The prepared cell growth scaffold is a porous cell growth scaffold that has no chemical crosslinking, and has a biological activity, a stable three-dimensional structure and a structural memory feature. The cell growth (Continued)

scaffold has an excellent biocompatibility and complete biodegradability, and supports the growth of cells and the growth of tissues and organs in vitro and in vivo, thereby being suitable for repair of human soft tissue traumas and defects.

2 Claims, 3 Drawing Sheets

(51) Int. Cl.
*A61L 27/52* (2006.01)
*A61L 27/58* (2006.01)
*A61L 27/56* (2006.01)
*A61L 27/48* (2006.01)

(52) U.S. Cl.
CPC .............. *A61L 27/48* (2013.01); *A61L 27/52* (2013.01); *A61L 27/56* (2013.01); *A61L 27/58* (2013.01); *A61L 27/362* (2013.01); *A61L 27/3608* (2013.01); *A61L 27/3612* (2013.01); *A61L 27/3616* (2013.01); *A61L 27/3629* (2013.01)

(56) References Cited

U.S. PATENT DOCUMENTS

| 2007/0031470 | A1 | 2/2007 | Kladakis et al. |
| 2010/0040687 | A1 | 2/2010 | Pedrozo et al. |
| 2010/0129463 | A1 | 5/2010 | Hiles et al. |
| 2010/0272782 | A1 | 10/2010 | Owens et al. |
| 2012/0263763 | A1 | 10/2012 | Sun et al. |
| 2013/0158658 | A1 | 6/2013 | Hayzlett |
| 2015/0037436 | A1 | 2/2015 | Huang et al. |

FOREIGN PATENT DOCUMENTS

| CN | 103108661 A | | 5/2013 | |
| CN | 103418001 A | | 12/2013 | |
| CN | 103432627 A | * | 12/2013 | ........... A61L 27/362 |
| CN | 103432627 A | | 12/2013 | |
| CN | 103520773 A | | 1/2014 | |
| CN | 104107456 A | | 10/2014 | |
| CN | 104144715 A | * | 11/2014 | ............ A61K 8/027 |
| CN | 104144715 A | | 11/2014 | |
| CN | 105169483 A | | 12/2015 | |
| EP | 1087756 B1 | | 8/2009 | |
| JP | 2010533042 A | | 10/2010 | |
| WO | 0110355 A1 | | 2/2001 | |
| WO | 2012006390 A1 | | 1/2012 | |
| WO | 2014181886 A1 | | 11/2014 | |

OTHER PUBLICATIONS

May 8, 2019, Office Action of Japanes Patent Application No. 2018-530120.

Nov. 13, 2018, Supplemental European Search Report of EP Application No. 16877807.4.

Dec. 12, 2019, Office Action of CN Application No. 201510986265.8.

* cited by examiner

METHOD FOR PREPARING CELL GROWTH SCAFFOLD HAVING STRUCTURAL MEMORY PROPERTIES

TECHNICAL FIELD

The present invention relates to a method for preparing a cell growth scaffold, which is a porous cell growth scaffold, that has no chemical crosslinking, and has a biological activity, a stable three dimensional structure and a structural memory feature, for use in the fields of material science, tissue engineering and regenerative medicine, in particular, to a method for preparing a cell growth scaffold having a structural memory property.

BACKGROUND OF THE RELATED ART

Since lesion, trauma and surgery often cause defects of soft tissues of a human body, regrowth of the soft tissues required for human bodies per se is a problem that needs to be solved by modern medicine. Various filling materials and dressings for repair of soft tissue defects, including a hydrogel and a porous sponge-type filling material prepared based on artificially synthesized polymer materials and natural biological materials have been developed at home and abroad. The collagen purified by acid treatment or enzyme treatment with animal tissues as raw materials, can be prepared into a collagen hydrogel, and the stability of the collagen in a hydrogel formulation can be enhanced by an appropriate chemical crosslinking treatment, so that the collagen is not easy to be degraded in vivo. The collagen suspension or hydrogel can be prepared into a porous collagen sponge material by freeze-drying, and by further chemical crosslinking fixing treatment, not only the stability of the collagen in the sponge material can be increased, but also the porous structural property of the collagen sponge material can be retained. The porous collagen sponge material is widely used in hemostasis of wound, filling of tissue defect sites and drug carrier, etc. in the clinical medicine.

Chinese patent literatures CN1235947C and CN101549171B provide specific methods for preparing such collagen sponge materials, respectively. Wherein, the technical solution provided in the patent literature CN1235947C is soaking animal tissues (skin, cartilage, sinew, tendon, etc.) containing rich collagen with a hydrochloric acid or acetic acid solution at room temperature, obtaining an extracellular collagen mesh of the animal tissues after enzymolysis, obtaining a collagen suspension by grinding and homogenization treatment, and placing the collagen suspension into a mold, to prepare a collagen sponge filler by extrusion forming and freeze-drying, in which treatment with a chemical crosslinker is used before or after the freeze-drying. Patent literature CN101549171B proposes that, after the high purity type II collagen solution is extracted, the type II collagen solution is concentrated with polyethylene glycol, and then the concentrated type II collagen is crosslinked with a crosslinker containing carbodiimide and N-hydroxysuccinimide, and freeze-dried to produce a collagen sponge.

The above technical solutions both obtain a collagen sponge by means of chemical crosslinking, but the shortcomings are obvious: the collagen sponge prepared by acidification and enzymolysis has drawbacks such as poor stability, lack of biological activity and rapid degradation.

In addition, in the technical field, other biological macromolecule materials such as sodium hyaluronate, chitosan, chitin, chondroitin sulfate are also added in the preparation of a collagen sponge to prepare a composite sponge material and the biological properties of the collagen sponge are improved. For example, Chinese patent literature CN101862475B discloses a technical solution that sodium hyaluronate is added into the collagen solution, followed by chemical crosslinking to prepare a composite collagen material. In Chinese patent literature CN103007336A, chitosan is added into the fishskin collagen and after freeze-drying and crosslinking, the material is freeze-dried again to prepare a fishskin collagen-based composite sponge. Although the stability of the collagen sponge was enhanced by chemical crosslinking treatment, and the collagen sponge composite material containing other biological macromolecules such as hyaluronic acid and chitosan has better biological activity, the stability of these sponge materials is still significantly decreased after radiation sterilization, and a relatively severe inflammation is prone to occur in large-area soft tissue filling or wound repair.

While the above technical solution enhances the stability of the collagen sponge by way of a chemical crosslinking, and the collagen sponge composite material containing other biological macromolecules such as hyaluronic acid and chitosan has better biological activity, there is still a problem in practice that the stability of these sponge materials is significantly decreased after the radiation sterilization, especially, a relatively severe inflammation is prone to occur in large-area soft tissue filling or wound repair.

US patent literature US2012/0263763A1 describes a fibrotic acellular tissue matrix-based sponge material. A method for preparing this material is to prepare a tissue matrix sponge material with pigskin as a raw material, followed by fat removal, ultracryotomy, decellularization and antigen removal, cleaning, fibrotic homogenate, virus inactivation, sterilization, and freeze-drying the acellular matrix suspension, the freeze-dried sponge material can be sterilized with oxirane or radiation. The positive effect generated from this method is to make this extracellular tissue matrix material better retain the basic structural features of the original tissue matrix without using chemical crosslinking; in addition to the collagen component, other important extracellular tissue matrix components, such as elastin, fibronectin and proteoglycan, are also contained; with no acid treatment and enzymolysis treatment in the preparation process, this sponge material has good biocompatibility, supports the rapid growth of host cells, and has better collagen stability, thereby reducing inflammatory response. However, the existing problem is that this sponge material obtained by this method has poor structure strength and elasticity, is prone to be crushed and deformed after being pressed, and cannot maintain the original material structure and recover to the original shape.

By summarizing the technical methods disclosed in the above literatures, the significant problem is: no matter whether to use the collagen hydrogel purified after acidolysis or enzymolysis, or to use the tissue matrix material suspension homogenized after decellularization, when a porous collagen sponge material is prepared, the prior art is firstly freeze-drying the hydrogel or suspension, followed by further chemically crosslinking treatment to enhance the mechanical strength of the material and increase the stability of the collagen in the sponge material, the chemical crosslinking treatment makes the tissue matrix material lose many excellent natural characteristics inherently possessed by the porous cell growth scaffold.

Content of the Invention

The technical problem to be solved in the present invention is to provide a method for preparing a cell growth scaffold having a structural memory property, the scaffold prepared by this method not only has an excellent biocompatibility and complete biodegradability but also supports the growth of cells and the growth of tissues and organs in vivo and in vitro.

Therefore, the technical solution solving said problem in the present invention is: a method for preparing a cell growth scaffold having a structural memory property, wherein, the method comprises: step 1, raw material collection: collection of a biological tissue raw material for preparing an acellular tissue matrix material, said raw material including, but not limited to, skin, cartilage, blood vessel, meniscus, stomach, small intestine, large intestine, diaphragm, tendon, ligament, nervous tissue, bladder and urethra of a human body or animal, a tissue rich in collagen being cut and separated out, into 1-20 mm little pieces or little sheets; step 2, raw material disinfection: soaking the little pieces or little sheets obtained in step 1 with 2% sodium carbonate for 4-48 hours or with other alkaline solution with pH of 10.5-12.5; step 3, decellularization treatment: decellularization treating the little pieces or little sheets soaked in step 2 with 0.1-2.0% sodium deoxycholate, octylphenylpolyethylene glycol, or with 10-200 units per litre of dispase for 4-36 hours; step 4, rinse of an acellular tissue matrix material: after the decellularization treatment in step 3, rinsing the little pieces or little sheets with 1-6 litre of normal saline or other neutral isosmotic solution per kilogram material for 2-5 times, each for 1-12 hours; step 5: mincing the acellular tissue matrix: after the rinse of the acellular tissue matrix material in step 4, mincing the little pieces or litter sheets with a mincer to grind the acellular tissue matrix material into a micro-fibrous or flocculent acellular tissue matrix material; step 6, acidification treatment: soaking a part of the micro-fibrous or flocculent acellular tissue matrix material obtained in step 5 in a 5-200 mM of hydrochloric acid or acetic acid solution with pH adjusted to 2.8-3.5 to perform the acidification treatment for 1-24 hours, further mincing and grinding the matrix material into particles in the form of hydrogel, and adjusting pH to 4.0-6.5 with a sodium hydroxide solution so as to obtain an acidification-treated acellular tissue matrix material in the form of hydrogel; step 7, mixing and injection molding: uniformly mixing another part of the micro-fibrous or flocculent acellular tissue matrix material obtained in step 5 in a dry weight mass proportion of 60-90% with the acidification-treated acellular tissue matrix material in the form of hydrogel in a dry weight mass proportion of 40-10% at the room temperature of 20-30° C., and then injecting the another part of the micro-fibrous or flocculent acellular tissue matrix material and the acidification-treated acellular tissue matrix material in the form of hydrogel, which are mixed, into a packaging mold; step 8, freezing treatment: placing the mold containing an acellular tissue matrix material suspension into a freezer at −20° C. or less for deep freezing, or further deep-freezing after the first thawing to increase the pore structure of the suspension; step 9, radiation treatment: treating the deep-frozen material with X-ray, gamma ray or electron beam; step 10, preparing the micro-fibrous or flocculent acellular tissue matrix material and the acidification-treated acellular tissue matrix material in the form of hydrogel treated in step 9 into a solid, porous cell growth scaffold profile that has no chemical crosslinking, and has a biological activity, a stable three dimensional structure and a structural memory feature. And the acellular tissue matrix material of the porous cell growth scaffold in said step 10 comprises a micro-fibrous or flocculent acellular tissue matrix material having a fibre diameter of 2-250 microns and a length of 100-3000 microns and an acidification-treated acellular tissue matrix material in the form of hydrogel having a particle diameter of 2-150 microns. The content of the total acellular tissue matrix materials in the matrix material is 10-100 mg/cm$^3$, the total porosity of said cell growth scaffold is 90-99%, and, the porosity of said cell growth scaffold with pore size larger than 25 microns is 80-98%. The micro-fibrous or flocculent acellular tissue matrix material in said scaffold accounts for 60%-90% by dry weight mass proportion, and said acidification-treated acellular tissue matrix material in the form of hydrogel accounts for 40%-10% by dry weight mass proportion.

As compared with the prior art, the growth scaffold prepared by the preparation method provided in the present invention is a porous cell growth scaffold having no chemical cross-linking and having a biological activity, a stable three dimensional structure and a structure memory property, which is a porous material having a special property that is prepared by mixing, in a certain proportion, a fibrous or flocculent tissue material and an acidified hydrogel material, followed by freezing/thawing and extruding and radiation processes. This scaffold not only has an excellent biocompatibility and complete biodegradability but also supports the growth of cells as well as the growth of tissues and organs in vivo and in vitro, thereby being suitable for repair of human soft tissue traumas and defects.

DETAILED DESCRIPTION OF EMBODIMENTS

Figure 5:
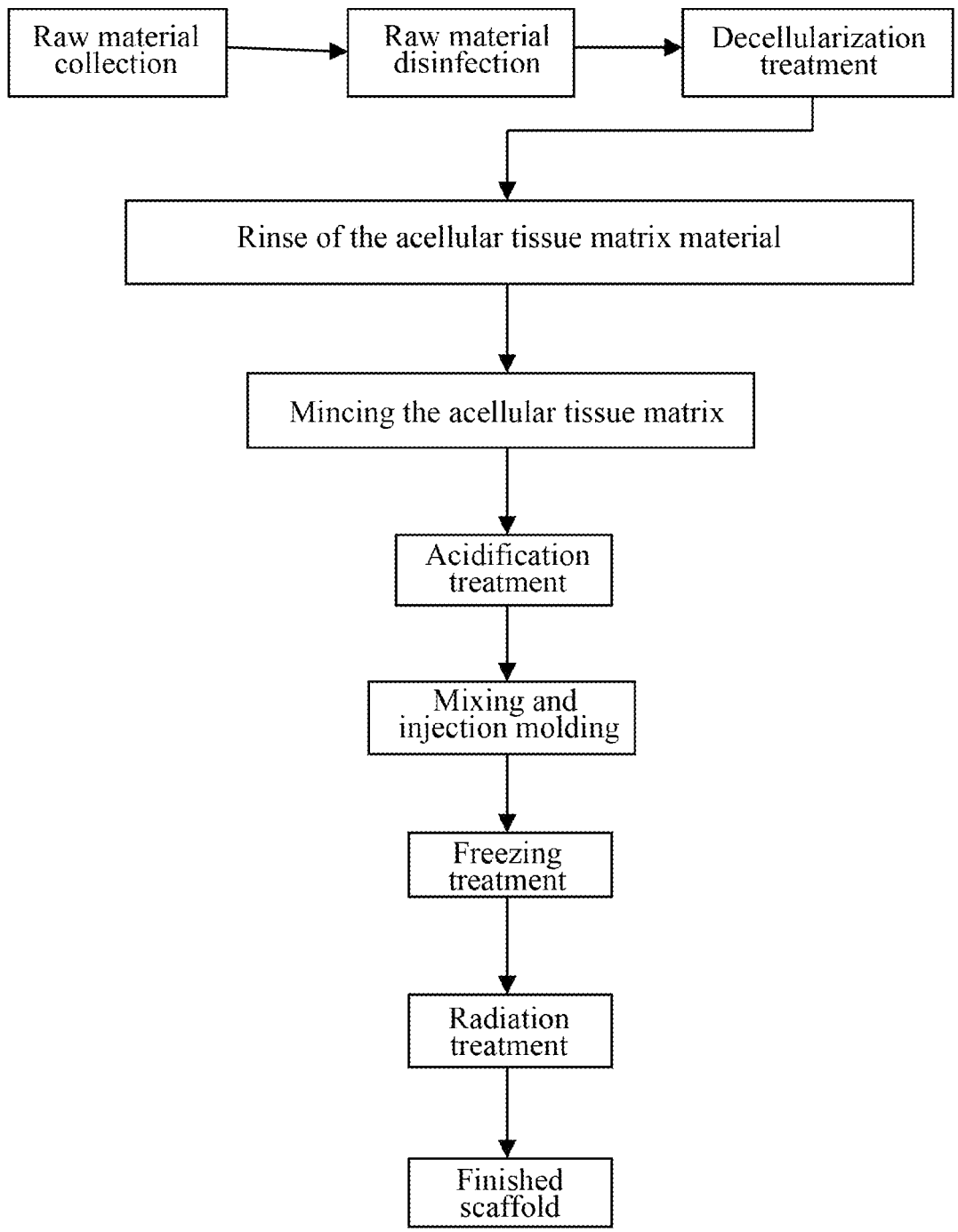
FIG. 5 is a flowchart for preparing the cell growth scaffold having the structural memory property in the present invention.

Referring to FIG. 5, the present invention relates to a method for preparing a cell growth scaffold having a structural memory property, the method comprising: step 1, raw material collection: collection of a biological tissue raw material for preparing an acellular tissue matrix material, said raw material including, but not limited to, skin, cartilage, blood vessel, meniscus, stomach, small intestine, large intestine, diaphragm, tendon, ligament, nervous tissue, bladder and urethra of a human body or animal, a tissue rich in collagen being cut and separated out, into 1-20 mm little pieces or little sheets; step 2, raw material disinfection: soaking the little pieces or little sheets obtained in step 1 with 2% sodium carbonate for 4-48 hours or with other alkaline solution with pH of 10.5-12.5; step 3, decellularization treatment: decellularization treating the little pieces or little sheets soaked in step 2 with 0.1-2.0% sodium deoxycholate, octylphenylpolyethylene glycol, or with 10-200 units per litre of neutral enzyme for 4-36 hours; step 4, rinse of an acellular tissue matrix material: after the decellularization treatment in step 3, rinsing the little pieces or little sheets with 1-6 litre of normal saline or other neutral isosmotic solution per kilogram material for 2-5 times, each for 1-12 hours; step 5: mincing the acellular tissue matrix: after the rinse of the acellular tissue matrix material in step 4, mincing the little pieces or litter sheets with a mincer to grind the acellular tissue matrix material into a micro-fibrous or flocculent acellular tissue matrix material; step 6, acidification treatment: soaking a part of the micro-fibrous or flocculent acellular tissue matrix material obtained in step 5 in a 5-200 mM of hydrochloric acid or acetic acid solution with pH adjusted to 2.8-3.5 to perform the acidification treatment for 1-24 hours, further mincing and grinding the matrix material into particles in the form of hydrogel, and adjusting pH to 4.0-6.5 with a sodium hydroxide solution so as to obtain an acidification-treated acellular tissue matrix material in the form of hydrogel; step 7, mixing and injection molding: uniformly mixing another part of the micro-fibrous or flocculent acellular tissue matrix material obtained in step 5 in a dry weight mass proportion of 60-90% with the acidification-treated acellular tissue matrix material in the form of hydrogel in a dry weight mass proportion of 40-10% at the room temperature of 20-30° C., and then injecting the another part of the micro-fibrous or flocculent acellular tissue matrix material and the acidification-treated acellular tissue matrix material in the form of hydrogel, which are mixed, into a packaging mold; step 8, freezing treatment: placing the mold containing an acellular tissue matrix material suspension into a freezer at −20° C. or less for deep freezing, or further deep-freezing after the first thawing to increase the pore structure of the suspension; step 9, radiation treatment: treating the deep-frozen material with X-ray, gamma ray or electron beam; step 10, preparing the micro-fibrous or flocculent acellular tissue matrix material and the acidification-treated acellular tissue matrix material in the form of hydrogel treated in step 9 into a solid, porous cell growth scaffold profile that has no chemical crosslinking, and has a biological activity, a stable three dimensional structure and a structural memory feature. And the acellular tissue matrix material of the porous cell growth scaffold in said step 10 comprises a micro-fibrous or flocculent acellular tissue matrix material having a fibre diameter of 2-250 microns and a length of 100-3000 microns and an acidification-treated acellular tissue matrix material in the form of hydrogel having a particle diameter of 2-150 microns. The content of the total acellular tissue matrix materials in the matrix material is 10-100 mg/cm$^3$, the total porosity of said cell growth scaffold is 90-99%, and, the porosity of said cell growth scaffold with pore size larger than 25 microns is 80-98%. The micro-fibrous or flocculent acellular tissue matrix material in said scaffold accounts for 60%-90% by dry weight mass proportion, and said acidification-treated acellular tissue matrix material in the form of hydrogel accounts for 40%-10% by dry weight mass proportion.

Figure 1:
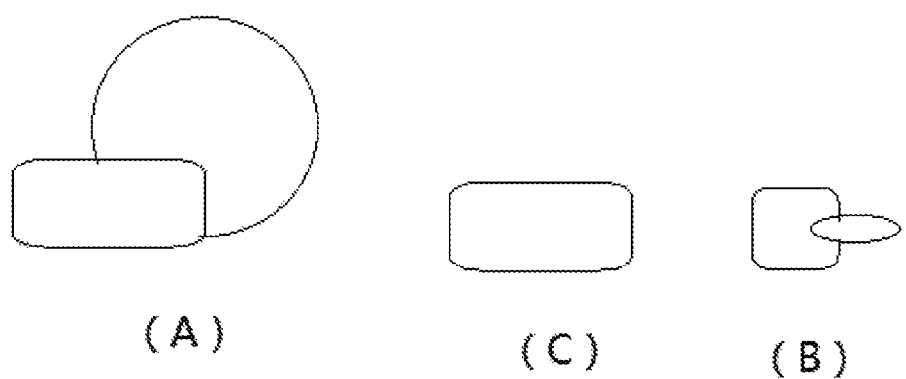
FIG. 1 is a schematic structural diagram of one example of the present invention.

For example, FIG. 1 shows a schematic diagram of the morphological structure of some products involved in the present invention, wherein, (A) in the figure is a disc-shaped and cylinder-shaped cell growth scaffold; (B) in the figure is a pillar-shaped cell growth scaffold with a diameter of 1.8 cm and a height of 3.0 cm, which is in the contraction state under a pressure action (pinched by fingers); (C) in the figure is the scaffold which is recovered to the original, stable three dimensional structure and shape after the pressure (pinched by fingers) is released. Specifically, the prepared cell growth scaffold contains 43 mg of acellular matrix material per cubic centimeter, i.e., the dry weight content of the tissue matrix is 4.3%. The cell growth scaffold has good elasticity, the cylinder-shaped scaffold with a diameter of 1.8 cm and a height of 3.0 cm can be contracted to a height of 5 mm under the pressure action, can be completely recovered to the original, stable three dimensional structure and shape after the pressure is released, and would not be deformed under multiple repeated pressures.

Figure 2:
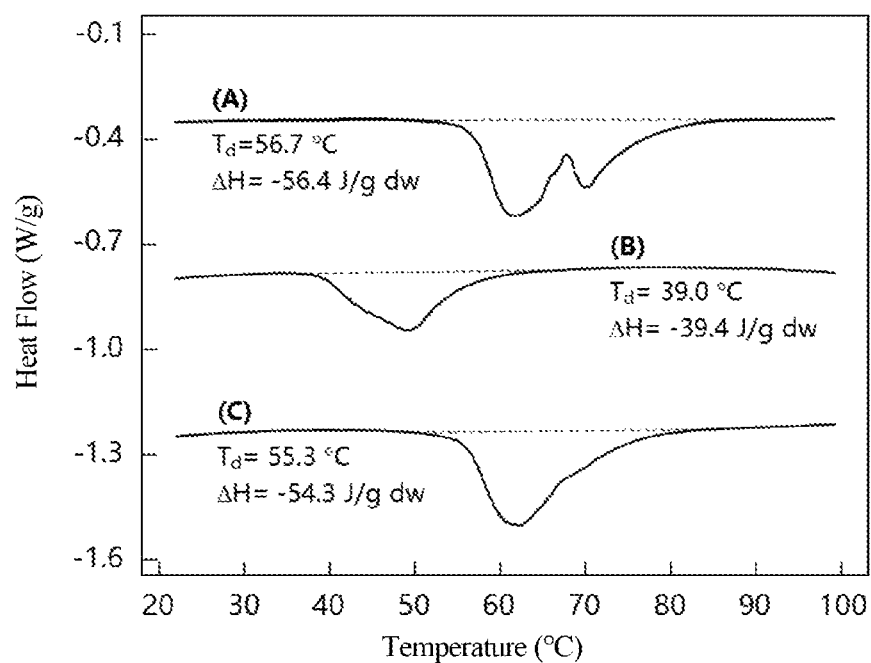
FIG. 2 are thermograms of differential scanning calorimetry (DSC) of the scaffold product in FIG. 1.

For example, FIG. 2 are thermograms of differential scanning calorimeter (DSC) of the tissue matrix material after being decellularized by a 0.5% sodium deoxycholate solution; wherein, (A) in the figure is a micro-fibrous or flocculent acellular tissue matrix material; (B) in the figure is an acellular tissue matrix hydrogel-like particles after being treated by a 50 mM acetic acid solution; (C) in the figure is a cell growth scaffold prepared from 70% of micro-fibrous acellular tissue matrix material and 30% of acidification-treated hydrogel-like particles. Specifically, differential scanning calorimeter (DSC) was used to compare and measure the thermal stability property of the materials: (A) the micro-fibrous or flocculent tissue matrix material, (B) the acidification-treated hydrogel-like tissue matrix material, (C) the cell growth scaffold prepared from 70% of micro-fibrous acellular tissue matrix material in a dry weight proportion and 30% of acidification-treated hydrogel-like particle in a dry weight proportion. The initial denaturation temperature of the micro-fibrous or flocculent tissue matrix material is 56.7° C., the thermal enthalpy value is −56.4 J/gdw (gram dry weight); the initial denaturation temperature of hydrogel-like tissue matrix material after acidification treatment is 39.0° C., the thermal enthalpy value is −39.4 J/gdw, suggesting that triple helical structure of collagen after the acidification treatment has expanded to be loose and unstable; the initial denaturation temperature of the finally prepared cell growth scaffold is 55.3° C., the thermal enthalpy value is −54.3 J/gdw, basically retaining the stability of the extracellular matrix material of the natural pig dermis.

Figure 3:
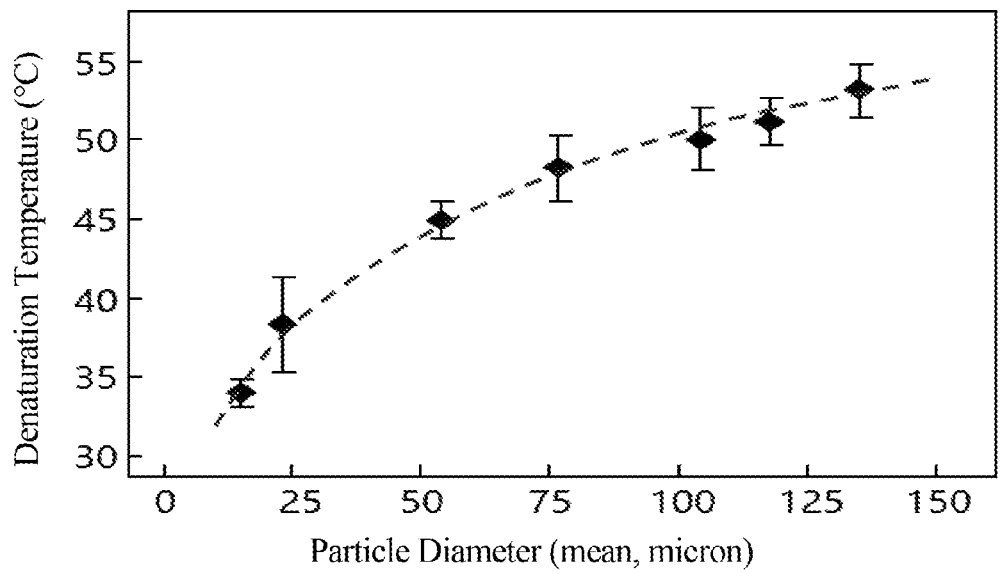
FIG. 3 is a curve showing the relationship between the stability and the particle diameter of two materials forming the scaffold product.

For example, FIG. 3 is a curve showing the relationship between the stability and particle diameter of the acellular tissue matrix hydrogel-like particles after the decellularization treatment by a 0.5% sodium deoxycholate solution and the treatment by a 50 mM acetic acid. Specifically, the stability of the acellular tissue matrix hydrogel-like particles after being treated by 50 mM acetic acid is associated with the particle diameter (FIG. 3). When the mean particle diameter is decreased from 140 microns to about 15 microns, the initial denaturation temperature is decreased from 55° C. to 35° C., which is lower than the normal body temperature of human. The smaller the hydrogel-like particle is, the worse the thermal stability is.

In combination with the above figures, it can be clearly seen how a cell growth scaffold having a structural memory property that is widely used in the fields of general surgery, orthopedics, plastic surgery, tissue engineering and regenerative medicine, etc. is achieved by the preparation method of the present invention.

To be more specific, the so-called matrix material for cell growth is a material consisting of two acellular tissue matrix materials having different properties in a certain proportion, i.e., the raw materials are derived from, but not limited to, skin, cartilage, blood vessel, meniscus, stomach, small intestine, large intestine, diaphragm, tendon, ligament, nervous tissue, bladder and urethra, etc. of the human body or animal. The tissue rich in collagen is cut and separated out, into 1-20 mm little pieces or little sheets. After two acellular tissue matrix materials having different properties are obtained, the cell growth scaffold having the structural memory property can be produced. For example, firstly, the tissue structure problem of the biological cell growth scaffold is solved, said scaffold in this example is formed by mixing, in the respective dry weight mass proportions, a micro-fibrous or flocculent acellular tissue matrix material having a fibre diameter of 2-250 microns and a length of 100-3000 microns with an acidification-treated hydrogel-like acellular tissue matrix material having a particle diameter of 2-150 microns, followed by injection molding, freezing, compressing, radiation, re-interweaving processes, in which, the matrix material for cell growth is the matrix material for cell growth scaffold, the content of the total acellular tissue matrix materials in the matrix material for the cell growth scaffold should be defined within a range of 10-100 mg/cm$^3$, the total porosity of said cell growth scaffold is 90-99%, and, the porosity of said cell growth scaffold with pore size larger than 25 microns is in the range of 80-98%. During the production of the cell growth scaffold, the preferred solution is adjusting the ratio of the micro-fibrous or flocculent acellular tissue matrix material to be 60%-90% by the dry weight mass proportion, and the acidification-treated hydrogel-like acellular tissue matrix material to be 40%-10% by the dry weight mass proportion, in the scaffold; in the injection molding process, the micro-fibrous or flocculent acellular tissue matrix material and the acidification-treated hydrogel-like acellular tissue matrix material should be uniformly mixed into a suspension and then injected into a mold; in the freezing process, the mixed suspension in the mold can be produced into an ice crystal only under the condition of at most −20° C. and after the radiation treatment by gamma ray, or a freezing procedure is finished by a process for freeze-thawing the mixed suspension in the mold for at least two times; in extruding and re-interweaving processes, the ice crystal should be extruded to re-interweave the micro-fibrous or flocculent acellular tissue matrix material and the acidification-treated hydrogel-like acellular tissue matrix granular material in the suspension together to produce a porous cell growth scaffold material having a stable three dimensional structure and a structure memory property. Only after undergoing the above processes can a porous cell growth scaffold material having a stable three dimensional structure and a structure memory feature be produced into scaffold products in various shapes.

EXAMPLES

Example 1, fresh pigskin was collected from a newly slaughtered and dehaired pig body, fat and epidermis were mechanically removed, and dermis with a thickness of about 1.5 mm was taken. After the blood and other dirt in the skin were washed away, the remaining hair on the skin was manually pulled out. The pig dermis was cut into a little piece with a length of about 1 cm and a width of about 1 cm, and rinsed with purified water. 200 g of dermis raw material was weighed and placed in a 1 L high density polypropylene bottle, to which was added a 800 mL of alkaline solution containing 2% sodium carbonate and 10 mM sodium hydroxide, and treated on a shaking bed for 20 hours (pH=12.5). After being treated with the alkaline solution, a 0.5 M acetic acid solution was used to perform acid-base neutralization. The solution after neutralization was poured out, 800 mL of 5 mM hydroxyethylpiperazine ethane sulfonic acid buffer solution (pH=7.5) containing 0.5% sodium deoxycholate and 5 mM ethylenediamine tetraacetic acid disodium was added, and treated on the shaking bed at room temperature overnight (about 20 hours) for decellularization. The little piece of dermis material that had undergone the decellularization treatment was rapidly rinsed with sterile normal saline twice, each for 30-60 minutes. The little piece of dermis material was ground with a high-speed grinder, to prepare a fine acellular tissue matrix material, so that the average width of the tissue particles was between 500-2000 microns and the length was between 2000-5000 microns. The matrix material was collected using a centrifugal method, and the upper supernatant was poured out. Sterile normal saline was added, so that the matrix material that was centrifuged and settled was suspended, and the matrix material was centrifuged and rinsed again. 800 mL of 0.1% peroxyacetic acid solution was added for treatment for 60 minutes. The matrix material was centrifuged and collected. The matrix material was washed with sterile normal saline by suspending, shaking, centrifuging and collecting twice, each for 30-60 minutes. 500 mL of 10 mM ethylenediamine tetraacetic acid disodium phosphate buffer solution (pH=7.5) per 50 g of matrix material was added, and ground and minced with the high-speed grinder, to prepare a microfibrous or flocculent acellular tissue matrix material, so that the diameter of the microfiber was between 2-250 microns and the length was between 100-3000 microns. By centrifuging, the supernatant was poured out, and the matrix microfiber material centrifuged and settled was collected. The micro-fibrous or flocculent matrix material was suspended in 0.9% saline, to obtain an extracellular tissue matrix material suspension, in which the content of the microfiber matrix material in the suspension was 4.9%. Then, some micro-fibrous or flocculent matrix material was taken, and acetic acid was added thereto, so that the final concentration of acetic acid was 50 mM. The matrix material was expanded by the acidification treatment, and then continually ground with the high-speed grinder, to prepare a hydrogel-like particle with a size of 10-250 microns, pH of the acidified hydrogel was adjusted to 6.5 with a sodium hydroxide solution, and the content of the hydrogel material was 1.5%. The micro-fibrous or flocculent tissue matrix material and acidification-treated hydrogel-like tissue matrix material were mixed in a ratio of 70% to 30% by dry weight. The mixed matrix material suspension was added into a disc-shaped and cylinder-shaped mold, and frozen in a refrigerator at −20° C. A porous structure was formed by freezing. After freezing, 25 kGy gamma ray treatment was used, to prepare a cell growth scaffold which is stable, has a structural memory feature and can be stored at room temperature.

Figure 4:
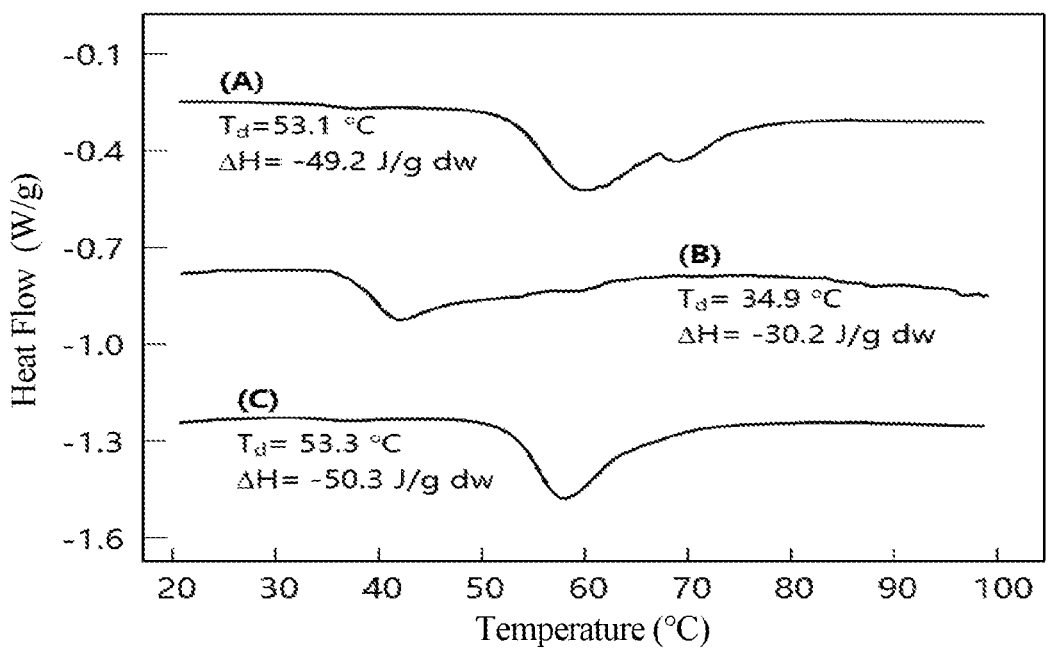
FIG. 4 are thermograms of differential scanning calorimetry of the scaffold product in FIG. 1.

Example 2, fresh pigskin was collected from a newly slaughtered and dehaired pig body, fat and epidermis were mechanically removed, after the blood and other dirt in the skin were washed away and the remaining tiny hair on the skin was manually pulled out, the pig dermis was cut into a little piece with a thickness of about 2 mm, a width of 1 cm and a length of 1 cm, and rinsed with purified water once, and 200 g raw material was weighed and placed in a high density polypropylene bottle. An alkaline solution (containing 2% sodium carbonate, 10 mM sodium hydroxide and 0.2% octylphenylpolyethylene glycol) was added and placed on a shaking bed for treatment in the alkaline solution for 20 hours. An acetic acid solution was added to perform the acid-base neutralization. 0.5% sodium lauryl sulfate (dissolved in 5 mM ethylenediamine tetraacetic acid disodium and 5 mM hydroxyethylpiperazine ethane sulfonic acid buffer solution) was added for decellularization, and oscillated on the shaking bed at room temperature for 20 hours. The material was rapidly rinsed with sterile normal saline twice, each for 30-60 minutes. The material was minced with a high-speed grinder, the material was minced to the size of a length of about 2.0-4.0 mm and a width of about 0.5-2.0 mm. The matrix material was centrifuged and collected, and the supernatant was poured out. The collected matrix material was soaked in a 0.1% peroxyacetic acid solution to treat for 2 hours, and rinsed with sterile normal saline for 1-2 times, each for 30-60 minutes. The material rinsed with the normal saline was rinsed with a 10 mM ethylenediamine tetraacetic acid disodium phosphate buffer solution, and ground and minced with the high-speed grinder, the material was minced to the size of a length of about 500-2500 mm and a width of about 50-500 mm, matrix microfiber was centrifuged and collected, and the supernatant was poured out. The matrix microfiber was suspended in 0.9% saline, to prepare and obtain an extracellular tissue matrix microfiber material suspension, in which the content of the material was 4.6%. One third of the microfiber material suspension was taken, and the material was diluted and acidized with a 50 mM acetic acid solution. The material that had undergone the acidification treatment was ground and minced with the high-speed grinder, to prepare a hydrogel material. The acidized hydrogel material was neutralized with a sodium hydroxide solution, with pH adjusted to 6.5, to prepare and obtain the hydrogel material with the content of 1.7%. The micro-fibrous or flocculent tissue matrix material and acidized hydrogel material were mixed in a ratio of 80% to 20% by dry weight, and the mixed matrix material was poured into a mold. After freezing in a refrigerator at −20° C., 25 kGy gamma ray treatment was used to prepare and obtain a biological tissue cell growth scaffold. As shown in FIG. 4, differential scanning calorimeter (DSC) was used to compare and measure the thermal stability property of the materials: (A) a micro-fibrous or flocculent tissue matrix material decellularized with 0.5% sodium lauryl sulfate, (B) an acidification-treated hydrogel-like tissue matrix material, (C) a cell growth scaffold prepared from 80% of micro-fibrous acellular tissue matrix material in a dry weight proportion and 20% of acidification-treated hydrogel-like particle in a dry weight proportion. The initial denaturation temperature of the micro-fibrous or flocculent tissue matrix material decellularized with 0.5% sodium lauryl sulfate is 53.1° C., the thermal enthalpy value is −49.2 J/gdw; the initial denaturation temperature of the hydrogel-like tissue matrix material after the acidification treatment is 34.9° C., the thermal enthalpy value is −30.2 J/gdw; the initial denaturation temperature of the finally prepared cell growth scaffold is 53.3° C., the thermal enthalpy value is −50.3 J/gdw, basically retaining the stability of the extracellular matrix material of the natural pig dermis.

What we claim is:

1. A method for preparing a cell growth scaffold having a structural memory property, wherein, the method comprises:
   step 1, raw material collection:
      collecting a biological tissue raw material for preparing an acellular tissue matrix material, said raw material comprising at least one of: skin, cartilage, blood vessel, meniscus, stomach, small intestine, large intestine, diaphragm, tendon, ligament, nervous tissue, bladder and urethra of a human body or animal,
      separating a tissue comprising collagen from the raw material, and cutting the tissue comprising collagen into 1-20 mm little pieces or little sheets:
   step 2, raw material disinfection:
      soaking the little pieces or little sheets obtained in step 1 with 2% sodium carbonate for 4-48 hours or with other alkaline solution with pH of 10.5-12.5;
   step 3, decellularization treatment:
      decellularization treating the little pieces or little sheets soaked in step 2 with 0.1-2.0% sodium deoxycholate, octylphenylpolyethylene glycol, or with 10-200 units per litre of neutral enzyme for 4-36 hours;
   step 4, rinse of an acellular tissue matrix material:
      after the decellularization treatment in step 3, rinsing the little pieces or little sheets with 1-6 litre of normal saline or other neutral isosmotic solution per kilogram material for 2-5 times, each for 1-12 hours;
   step 5: mincing the acellular tissue matrix:
      after the rinse of the acellular tissue matrix material in step 4, mincing the little pieces or litter sheets with a mincer to grind the acellular tissue matrix material into a micro-fibrous or flocculent acellular tissue matrix material;
   step 6, acidification treatment:
      soaking a part of the micro-fibrous or flocculent acellular tissue matrix material obtained in step 5 in a 5-200 mM of hydrochloric acid or acetic acid solution with pH adjusted to 2.8-3.5 to perform the acidification treatment for 1-24 hours,
      further mincing and grinding the matrix material into particles in the form of hydrogel, and
      adjusting pH to 4.0-6.5 with a sodium hydroxide solution so as to obtain an acidification-treated acellular tissue matrix material in the form of hydrogel;
   step 7, mixing and injection molding:
      uniformly mixing another part of the micro-fibrous or flocculent acellular tissue matrix material obtained in step 5 in a dry weight mass proportion of 60-90% with the acidification-treated acellular tissue matrix material in the form of hydrogel in a dry weight mass proportion of 40-10% at the room temperature of 20-30° C., and
      then injecting the another part of the micro-fibrous or flocculent acellular tissue matrix material and the acidification-treated acellular tissue matrix material in the form of hydrogel, which are mixed, into a packaging mold;
   step 8, freezing treatment:
      placing the mold containing an acellular tissue matrix material suspension into a freezer at −20° C. or less for deep freezing;
   step 9, radiation treatment:
      treating the deep-frozen material with X-ray, gamma ray or electron beam to produce a porous cell growth scaffold.

2. A porous cell growth scaffold, prepared by the method of claim 1.

* * * * *